United States Patent
Ito et al.

(10) Patent No.: US 9,815,799 B2
(45) Date of Patent: Nov. 14, 2017

(54) SURFACE-MODIFYING AGENT AND ARTICLE USING SAME

(71) Applicant: Dexerials Corporation, Shinagawa-ku, Tokyo (JP)

(72) Inventors: Makiya Ito, Kanuma (JP); Kenji Kobayashi, Kanuma (JP); Nobuo Tano, Kanuma (JP); Kyungsung Yun, Tokyo (JP)

(73) Assignee: DEXERIALS CORPORATION, Shinagawa-ku, Tokyo (JP)

( * ) Notice: Subject to any disclaimer, the term of this patent is extended or adjusted under 35 U.S.C. 154(b) by 0 days.

(21) Appl. No.: 15/119,799

(22) PCT Filed: Feb. 17, 2015

(86) PCT No.: PCT/JP2015/054902
§ 371 (c)(1),
(2) Date: Aug. 18, 2016

(87) PCT Pub. No.: WO2015/129593
PCT Pub. Date: Sep. 3, 2015

(65) Prior Publication Data
US 2017/0050940 A1    Feb. 23, 2017

(30) Foreign Application Priority Data
Feb. 27, 2014    (JP) ................ 2014-036967

(51) Int. Cl.
| | |
|---|---|
| *C07D 251/52* | (2006.01) |
| *C08G 65/00* | (2006.01) |
| *C08G 65/333* | (2006.01) |
| *C08G 18/50* | (2006.01) |
| *C08G 18/81* | (2006.01) |
| *C09D 175/16* | (2006.01) |
| *C09D 7/12* | (2006.01) |
| *C09D 5/16* | (2006.01) |

(52) U.S. Cl.
CPC ....... *C07D 251/52* (2013.01); *C08G 18/5063* (2013.01); *C08G 18/5066* (2013.01); *C08G 18/8116* (2013.01); *C08G 65/007* (2013.01); *C08G 65/33317* (2013.01); *C08G 65/33351* (2013.01); *C09D 5/1637* (2013.01); *C09D 7/125* (2013.01); *C09D 7/1233* (2013.01); *C09D 175/16* (2013.01)

(58) Field of Classification Search
CPC .................................................. C07D 251/52
See application file for complete search history.

(56) References Cited

U.S. PATENT DOCUMENTS

2004/0181008 A1*  9/2004  Hanazawa ......... C08G 18/2885
                                                      524/589

FOREIGN PATENT DOCUMENTS

| JP | S62132850 A | 6/1987 |
|---|---|---|
| JP | 2001019736 A | 1/2001 |
| JP | 2005517081 A | 6/2005 |
| JP | 2008163475 A | 7/2008 |
| WO | 2003002628 A1 | 1/2003 |

OTHER PUBLICATIONS

May 19, 2015, International Search Report issued in the International Patent Application No. PCT/JP2015/054902.

* cited by examiner

*Primary Examiner* — Golam M M Shameem
*Assistant Examiner* — Laura Daniel
(74) *Attorney, Agent, or Firm* — Kenja IP Law PC

(57) ABSTRACT

Provided are a surface-modifying agent that enables production of a coating film that preserves transparency of a substrate while displaying high water repellency and excellent stain resistance, particularly in terms of wipeability of oil-based ink, and also an article for which the surface-modifying agent is used. The surface-modifying agent includes a triazine skeleton, a (meth)acrylate group bonded to the triazine skeleton via an urethane bond, and a perfluoropolyether chain bonded to the triazine skeleton.

5 Claims, 4 Drawing Sheets

FIG. 3
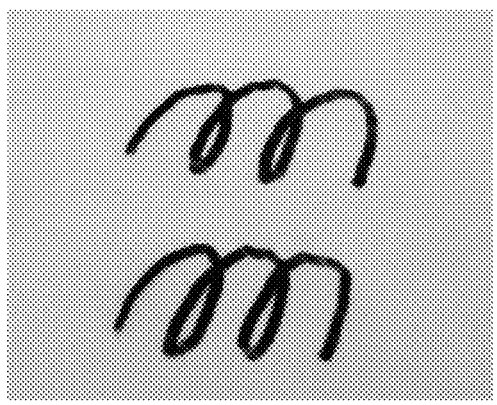
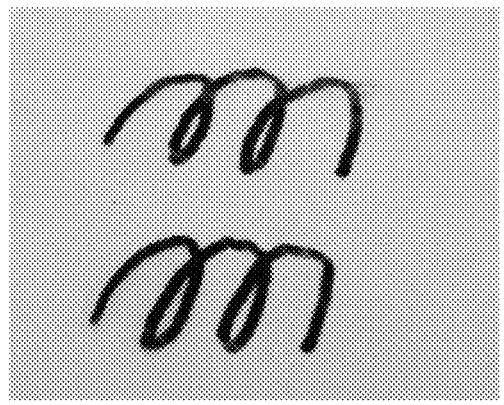
FIG. 4
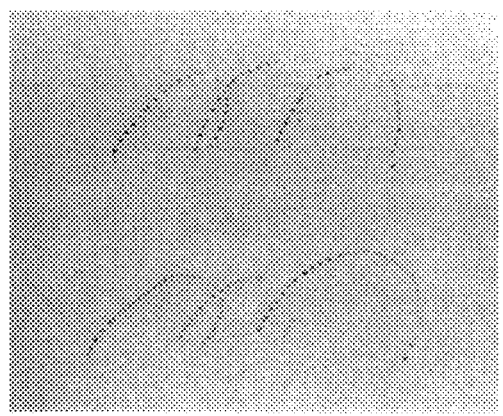
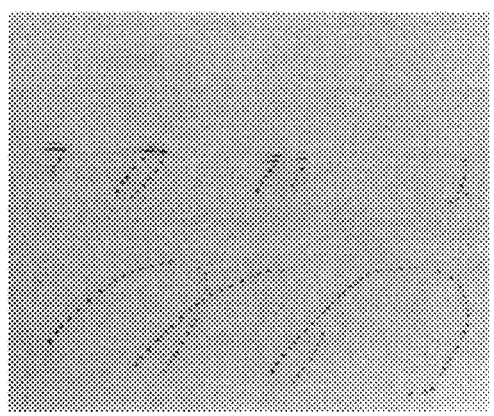
FIG. 5
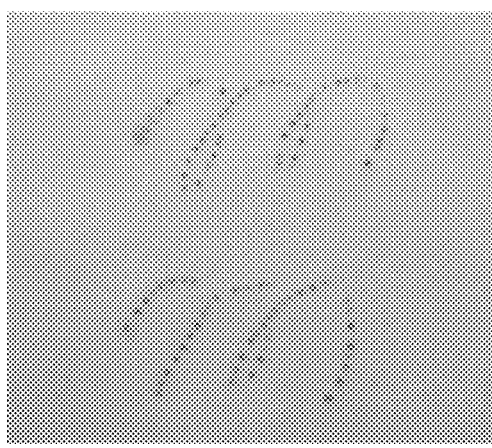
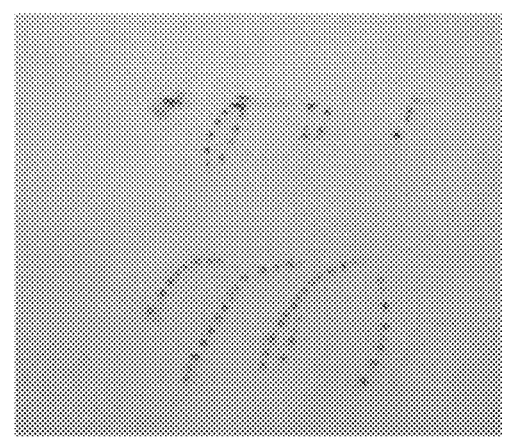

FIG. 6
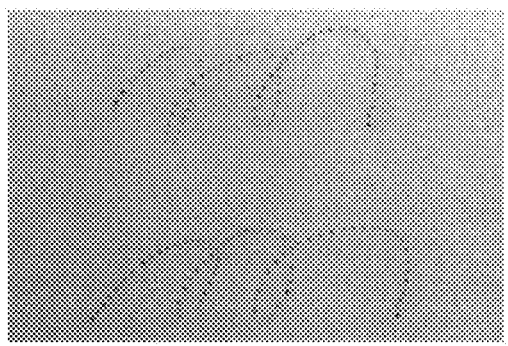
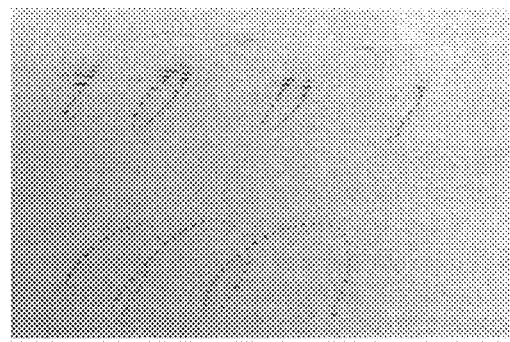
FIG. 7
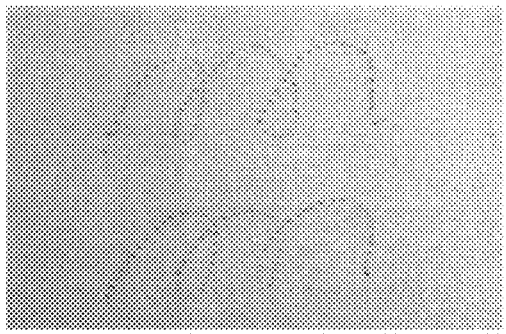
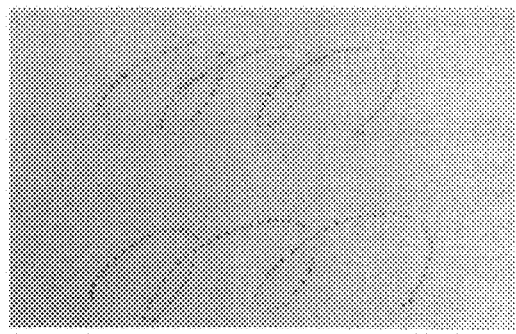

SURFACE-MODIFYING AGENT AND ARTICLE USING SAME

CROSS-REFERENCE TO RELATED APPLICATION

The present application claims priority of Japanese Patent Application No. 2014-036967 (filed on Feb. 27, 2014), the entire disclosure of which is incorporated into the present application by reference.

TECHNICAL FIELD

The present disclosure relates to a surface-modifying agent and an article for which this surface-modifying agent is used. In particular, the present disclosure relates to a surface-modifying agent including a triazine skeleton, a (meth)acrylate group bonded to the triazine skeleton via an urethane bond, and a perfluoropolyether chain bonded to the triazine skeleton, and to an article for which this surface-modifying agent is used.

In general, when a coating film is to be formed on the surface of any one of various types of substrates such as plastic, glass, fiber, metal, wood, or paper, it is common to blend a surface-modifying agent into a coating resin composition that is used to form the coating film with an objective of enhancing functionality of the coating film.

Examples of functions that the surface-modifying agent may be required to perform include improving surface hardness and enhancing scratch resistance.

Radiation curable resins are currently being favorably used as surface-modifying agents having functions such as described above. These radiation curable resins can maintain transparency even after curing, which is particularly advantageous in terms of preserving the external appearance of a transparent substrate, such as plastic.

In recent years, an increasingly wide range of functions have been demanded from coating films. Particularly, in addition to the properties and functions described above, there is strong demand for enhancement of water repellency and stain resistance.

In order to provide a surface-modifying agent that satisfies this demand, a number of radiation curable resins and compositions including these resins have been proposed that, compared to other radiation curable resin, are provided with a perfluoropolyether chain with an objective of improving stain resistance or a specific functional group with an objective of extending the life of this stain resistance.

In one example, an urethane acrylate having a poly(perfluoroalkylene)ether chain has been proposed that is obtained by reacting a polyisocyanate with a poly(perfluoroalkyleneether) having a hydroxy group, a monomer having a hydroxy group and an acroyl group, and so forth (for example, refer to PTL 1).

In another example, an urethane acrylate having a poly(perfluoroalkyleneether) chain has been proposed that is obtained by reacting a triisocyanate, prepared by trimerizing a diisocyante, with a poly(perfluoroalkyleneether) having a hydroxy group and a monomer having a hydroxy group and an acryloyl group (for example, refer to PTL 2).

However, the radiation curable resins described in PTL 1 and 2 still suffer from a problem of having inadequate stain resistance, particularly in terms of wipeability of oil-based ink adhering to the surface of a coating film.

CITATION LIST

Patent Literature

PTL 1: JP 2001-019736 A
PTL 2: WO 2003/002628 A1

SUMMARY

Technical Problem

The present disclosure aims to solve the various conventional problems described above and achieve the following objective. Specifically, an objective of the present disclosure is to provide a surface-modifying agent that enables production of a coating film that preserves transparency of a substrate while displaying high water repellency and excellent stain resistance, particularly in terms of wipeability of oil-based ink, and also to provide an article for which the surface-modifying agent is used.

Solution to Problem

The following is provided as a means of solving the problem described above. Specifically, the present disclosure provides:

<1> A surface-modifying agent including a triazine skeleton, a (meth)acrylate group bonded to the triazine skeleton via an urethane bond, and a perfluoropolyether chain bonded to the triazine skeleton.

In the surface-modifying agent described in <1>, inclusion of the perfluoropolyether chain has an effect of enabling improvement in stain resistance, particularly in terms of wipeability of oil-based ink, and bonding of the perfluoropolyether chain to the triazine skeleton has an effect of enabling high stain resistance due to the perfluoropolyether chain to be sufficiently expressed, particularly in terms of wipeability of oil-based ink.

<2> The surface-modifying agent described in <1> represented by formula (1) or (2) shown below,

[CHEM 1]

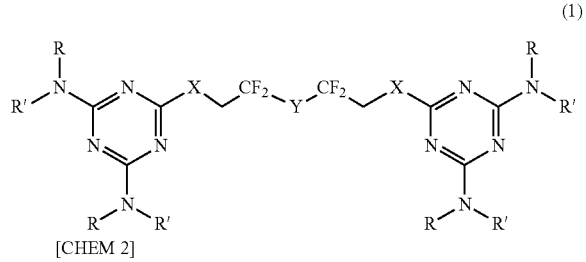

(1)

[CHEM 2]

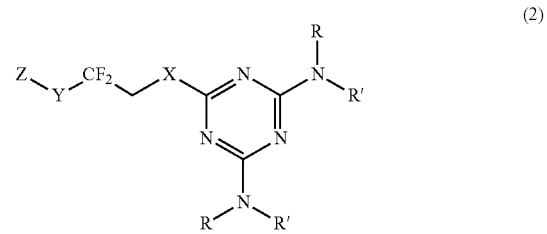

(2)

where, in the formulae (1) and (2):
—X— represents —O—, —N($R^1$)—, or —O—$CH_2CH_2$—O—, wherein $R^1$ represents hydrogen or an alkyl group;

—Y— represents a perfluoropolyether chain selected from the group consisting of —(OCF$_2$)$_n$—O—(CF$_2$CF$_2$O)$_m$—, —O—(CF$_2$CF$_2$O)$_p$—, —O—(CF$_2$CF$_2$CF$_2$O)$_q$—, and —O—(CF(CF$_3$)CF$_2$O)$_r$—, wherein m, n, p, q, and r each represent a positive integer, 0.8<m/n<3 is satisfied, and units composing —Y— may be bonded to one another in any order;

R and R' may represent the same or different structures each indicated by hydrogen, an alkyl group having a carbon number of 1-8, or —R$^2$—O—CO—NH—R$^3$, with at least one of R and R' being a structure indicated by —R$^2$—O—CO—NH—R$^3$, wherein R$^2$ represents an alkylene group having a carbon number of 2-8 and having a chain, branched, or ring shape, and R$^3$ represents —CH$_2$CH$_2$—OCO—CH=CH$_2$, —CH$_2$CH$_2$—OCO—C(CH$_3$)=CH$_2$, or —C(CH$_3$)—(CH$_2$—OCO—CH=CH$_2$)$_2$; and Z— represents CF$_3$—, CF$_3$—CF$_2$—O—, CF$_3$—CF$_2$—CF$_2$—, or CF$_3$—CF(CF$_3$)—O—.

<3> The surface-modifying agent described in <1> or <2>, wherein separate triazine skeletons are bonded to opposite ends of the perfluoropolyether chain.

<4> The surface-modifying agent described in <2>, wherein the perfluoropolyether chain represented by Y has a number-average molecular weight of 1,000 to 5,000.

<5> The surface-modifying agent described in any one of <1> to <4> represented by formula (3) shown below,

[CHEM 3]

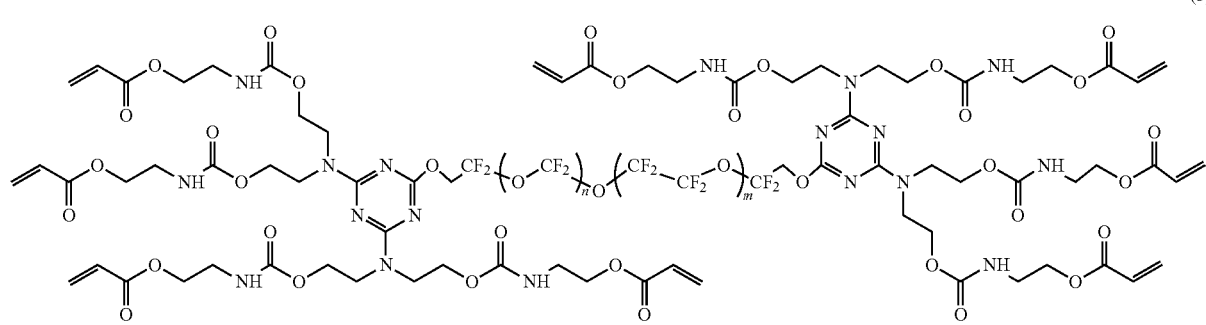

(3)

where, in the formula (3), m and n each represent a positive integer, 0.8<m/n<3 is satisfied, and —(OCF$_2$)—, —O—, and —(CF$_2$CF$_2$O)— composing —(OCF$_2$)$_n$—O—(CF$_2$CF$_2$O)$_m$— in the formula (3) may be bonded to one another in any order.

<6> An article comprising the surface-modifying agent described in any one of <1> to <5>.

Advantageous Effect

According to the present disclosure, it is possible to solve the various conventional problems described above and achieve the objective described above, and it is also possible to provide a surface-modifying agent that enables production of a coating film that preserves transparency of a substrate while displaying high water repellency and excellent stain resistance, particularly in terms of wipeability of oil-based ink, and to provide an article for which the surface-modifying agent is used.

BRIEF DESCRIPTION OF THE DRAWINGS

In the accompanying drawings:
FIG. 3 is a schematic diagram illustrating ink adhesion before and after wiping in a reference example;
FIG. 4 is a schematic diagram illustrating ink adhesion before and after wiping in Example 1;
FIG. 5 is a schematic diagram illustrating ink adhesion before and after wiping in Example 2;
FIG. 6 is a schematic diagram illustrating ink adhesion before and after wiping in Comparative Example 1;
and
FIG. 7 is a schematic diagram illustrating ink adhesion before and after wiping in Comparative Example 2.

Figure 1:
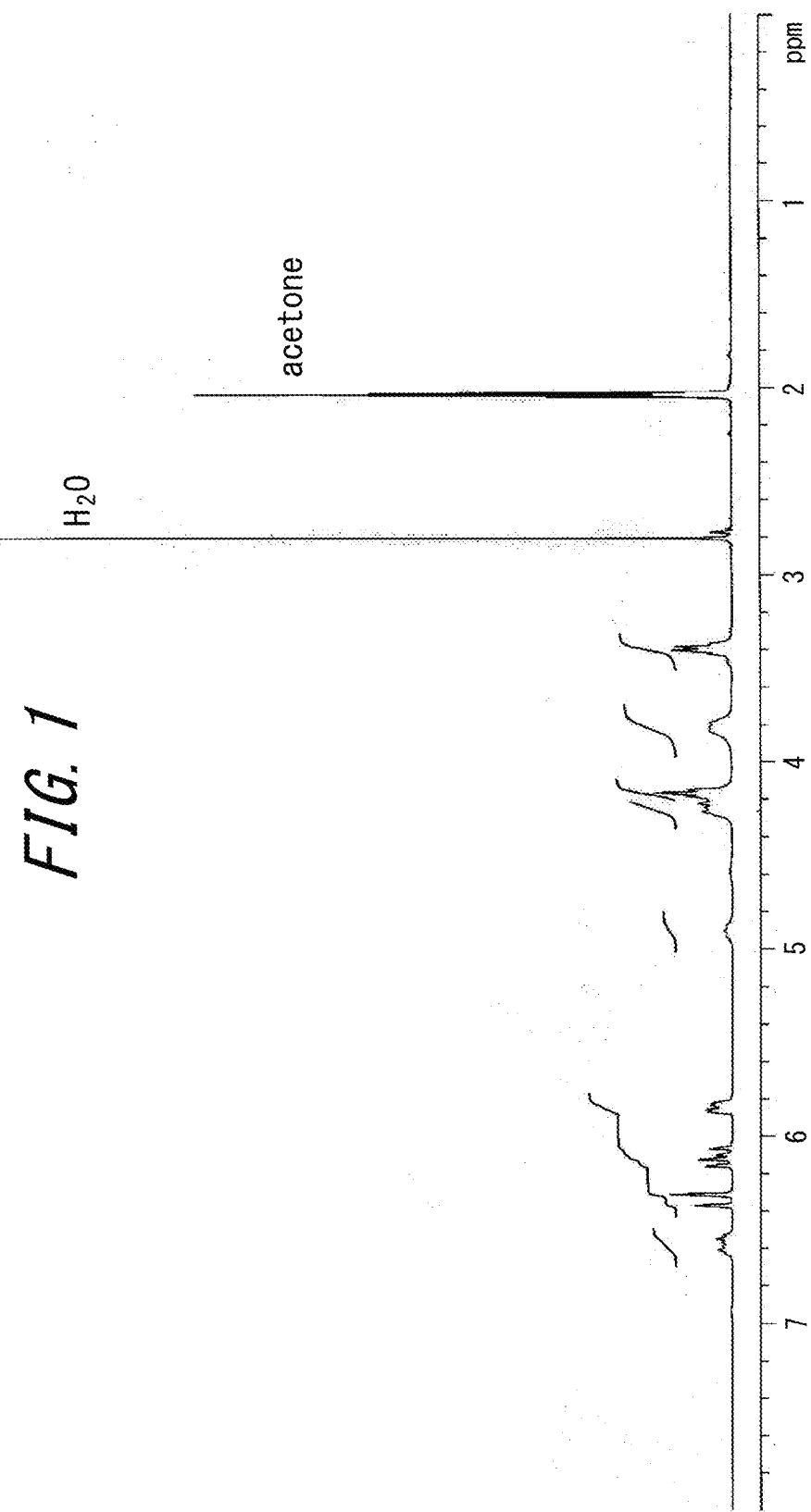
FIG. 1 is a chart of a $^1$H-NMR spectrum for a surface-modifying agent (A) in Example 1.

DETAILED DESCRIPTION (Surface-Modifying Agent)
A surface-modifying agent according to the present disclosure includes at least a triazine skeleton, a (meth)acrylate group bonded to the triazine skeleton via an urethane bond, and a perfluoropolyether chain bonded to the triazine skeleton, and may further include other parts as required.

<Triazine Skeleton>
The triazine skeleton can be appropriately selected depending on the objective, without any specific limitations other than being a skeleton that includes a triazine ring.

In a molecule of the surface-modifying agent, the triazine skeleton is adjacent to the perfluoropolyether chain, which is explained further below. This has an effect of enabling sufficient expression of high stain resistance due to the perfluoropolyether chain, particularly in terms of wipeability of oil-based ink.

It is preferable that separate triazine skeletons are bonded to opposite ends of the subsequently described perfluoropolyether chain. This enables an even greater degree of expression of oil-based ink wipeability. Herein, the statement that "separate triazine skeletons are bonded to opposite ends of the perfluoropolyether chain" is inclusive not only of a situation in which separate triazine skeletons are "directly bonded" to opposite ends of the perfluoropolyether chain, but also a situation in which separate triazine skeletons are "indirectly bonded" to opposite ends of the perfluoropolyether chain.

Inclusion of the triazine skeleton in the surface-modifying agent according to the present disclosure is advantageous in terms of enabling a higher degree of material design freedom.

<(Meth)Acrylate Group>

The term "(meth)acrylate group" refers to either an "acrylate group ($CH_2$=CH—COO—)" or a "methacrylate group ($CH_2$=C($CH_3$)—COO—)".

The (meth)acrylate group is bonded to the triazine skeleton via an urethane bond (—O—CO—NH—). This has an effect of strengthening chemical bonding to other components in a radiation curable resin composition when the surface-modifying agent according to the present disclosure is contained therein and of improving durability of the surface-modifying agent.

<Perfluoropolyether Chain>

The term "perfluoropolyether chain" refers to a chain including a plurality of ether bonds and one or more perfluoromethylene groups ($CF_2$). The perfluoropolyether chain may include other functional groups besides the ether bonds and the perfluoromethylene groups.

Inclusion of the perfluoropolyether chain in the surface-modifying agent according to the present disclosure has an effect of improving stain resistance, particularly in terms of wipeability of oil-based ink.

<Structure of Surface-Modifying Agent>

The structure of the surface-modifying agent can be appropriately selected depending on the objective, without any specific limitations other than being a structure that at least includes a triazine skeleton, a (meth)acrylate group bonded to the triazine skeleton via an urethane bond, and a perfluoropolyether chain bonded to the triazine skeleton. For example, the surface-modifying agent may have a structure indicated by formula (1) or (2) shown below.

Among such structures, the structure indicated by formula (1) shown below is preferable in terms of improving wipeability of oil-based ink and the structure indicated by formula (3) shown below is more preferable in terms of further improving wipeability of oil-based ink.

[CHEM 4]

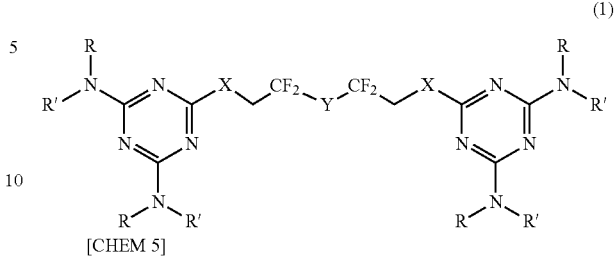

(1)

[CHEM 5]

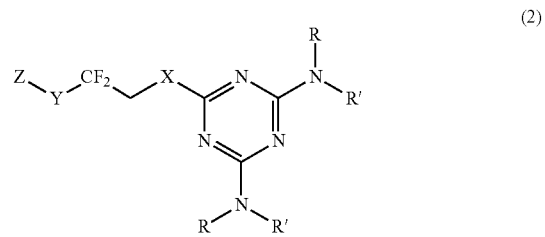

(2)

In formulae (1) and (2):

—X— represents —O—, —N($R^1$)—, or —O—$CH_2CH_2$—O—, wherein $R^1$ represents hydrogen or an alkyl group;

—Y— represents a perfluoropolyether chain selected from the group consisting of —(OCF_2$)_n$—O—($CF_2CF_2O)_m$—, —O—($CF_2CF_2O)_p$—, —O—($CF_2CF_2CF_2O)_q$—, and —O—(CF($CF_3$)$CF_2O)_r$—, wherein m, n, p, q, and r each represent a positive integer, 0.8<m/n<3 is satisfied, and units composing —Y— may be bonded to one another in any order;

R and R' may represent the same or different structures each indicated by hydrogen, an alkyl group having a carbon number of 1-8, or —$R^2$—O—CO—NH—$R^3$, with at least one of R and R' being a structure indicated by —$R^2$—O—CO—NH—$R^3$, wherein $R^2$ represents an alkylene group having a carbon number of 2-8 and having a chain, branched, or ring shape, and $R^3$ represents —$CH_2CH_2$—OCO—CH=$CH_2$, —$CH_2CH_2$—OCO—C($CH_3$)=$CH_2$, or —C($CH_3$)—($CH_2$—OCO—CH=$CH_2)_2$; and Z— represents $CF_3$—, $CF_3$—$CF_2$—O—, $CF_3$—$CF_2$—$CF_2$—, or $CF_3$—CF($CF_3$)—O—.

[CHEM 6]

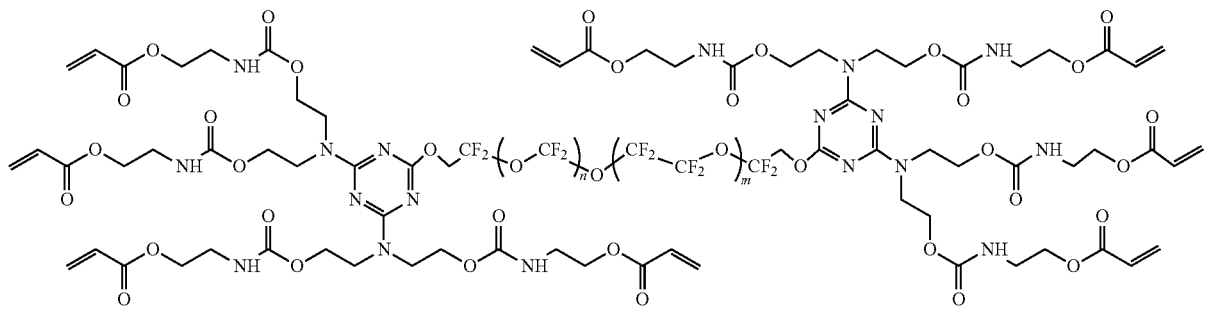

(3)

In formula (3), m and n each represent a positive integer, $0.8 < m/n < 3$ is satisfied, and $—(OCF_2)—$, $—O—$, and $—(CF_2CF_2O)—$ composing $—(OCF_2)_n—O—(CF_2CF_2O)_m—$ in formula (3) may be bonded to one another in any order.

In a situation in which $—X—$ in formula (1) or (2) is $—N(R^1)—$ and $R^1$ is an alkyl group, the alkyl group may be substituted or unsubstituted and has a carbon number of preferably 1-8, more preferably 1-4, and particularly preferably 1 or 2.

A carbon number of greater than 8 may lead to an increase in surface free energy and a decrease in water repellency. On the other hand, a carbon number in either the more preferable range or the particularly preferable range described above is advantageous in terms of improving water repellency.

In a situation in which $—Y—$ in formula (1) or (2) is a perfluoropolyether chain represented by $—(OCF_2)_n—O—(CF_2CF_2O)_m—$, the values of m and n can be appropriately selected depending on the objective, without any specific limitations other than m/n being greater than 0.8 and less than 3. Furthermore, as previously explained, $—(OCF_2)—$, $—O—$, and $—(CF_2CF_2O)—$ composing $—Y—$ may be bonded to one another in any order.

The number-average molecular weight of Y (perfluoropolyether chain) can be appropriately selected depending on the objective, without any specific limitations, and is preferably from 1,000 to 5,000, and more preferably from 2,000 to 4,000.

If the number-average molecular weight of Y is less than 1,000, the dynamic coefficient of friction may become excessively high and wipeability of oil-based ink may be negatively affected, whereas if the number-average molecular weight of Y is greater than 5,000, solubility in the radiation curable resin composition may decrease and the function as a surface-modifying agent may not be expressed. On the other hand, it is advantageous for the number-average molecular weight of Y to be in either the more preferable range or the particularly preferable range described above in terms of the dynamic coefficient of friction and solubility in the radiation curable resin composition.

In a situation in which R or R' in formula (1) or (2) is an alkyl group, the alkyl group may be substituted or unsubstituted and has a carbon number of preferably 1-8, more preferably 1-4, and particularly preferably 1 or 2.

A carbon number of greater than 8 may lead to an increase in surface free energy and a decrease in water repellency. On the other hand, it is advantageous for the carbon number to be in either the more preferable range or the particularly preferable range described above in terms of improving water repellency.

In a situation in which R or R' in formula (1) or (2) is indicated by $—R^2—O—CO—NH—R^3$, an alkylene group indicated by $R^2$ may be substituted or unsubstituted and has a carbon number of preferably 2-8, more preferably 2-4, and particularly preferably 2 or 3. It is advantageous for the carbon number to be in either the more preferable range or the particularly preferable range described above in terms of reducing production costs.

<Synthetic Method of Surface-Modifying Agent>

The method by which the surface-modifying agent is synthesized can be appropriately selected depending on the objective, without any specific limitations. For example, the synthetic method may be a method including (i) a first step of reacting a compound having a triazine skeleton with a perfluoropolyether to produce an intermediate compound 1, (ii) a second step of reacting the intermediate compound 1 with a compound including a hydroxy group and an amino group to produce an intermediate compound 2, and (iii) a third step of reacting the intermediate compound 2 with a compound having an isocyanate group and a (meth)acrylate group in the presence of a catalyst for an urethane-forming reaction.

—First Step—

The compound having a triazine skeleton that is used in the first step can be appropriately selected depending on the objective, without any specific limitations, and is for example commercially available cyanuric chloride.

The perfluoropolyether used in the first step can be appropriately selected depending on the objective, without any specific limitations, and is for example Fluorolink D (produced by Solvay Specialty Polymers Japan K.K.), Fluorolink D10H (produced by Solvay Specialty Polymers Japan K.K.), or Fluorolink D4000 (produced by Solvay Specialty Polymers Japan K.K.).

The reaction temperature in the first step can be appropriately selected depending on the objective, without any specific limitations, and is preferably from 0° C. to 40° C. from a viewpoint of preventing addition of two or more perfluoropolyether chains to the same triazine skeleton.

—Second Step—

The compound having a hydroxy group and an amino group used in the second step can be appropriately selected depending on the objective, without any specific limitations, and is for example diethanolamine, aminoethanol, 2-methylaminoethanol, 2-ethylaminoethanol, 2-propylaminoethanol, 2-butylaminoethanol, 2-t-butylaminoethanol, 2-pentylaminoethanol, or 2-hexylaminoethanol.

The reaction temperature in the second step can be appropriately selected depending on the objective, without any specific limitations, and is preferably from 0° C. to 100° C. from a viewpoint of efficiently carrying out an appropriate addition reaction.

—Third Step—

The compound having an isocyanate group and a (meth)acrylate group that is used in the third step can be appropriately selected depending on the objective, without any specific limitations, and is for example 2-isocyanatoethyl acrylate (2-acryloyloxyethyl isocyanate), 2-isocyanatomethyl methacrylate, or 1,1-(bisacryloyloxymethyl)ethyl isocyanate. Any one of these examples may be used or any two or more of these examples may be used in combination.

The catalyst for an urethane-forming reaction that is used in the third step can be appropriately selected depending on the objective, without any specific limitations, and is for example an organic tin compound such as dibutyltin dilaurate, dibutyltin diacetate, dibutyltin thiocarboxylate, dibutyltin dimaleate, dioctyltin thiocarboxylate, tin octenoate, or monobutyltin oxide; an inorganic tin compound such as stannous chloride; an organic lead compound such as lead octenoate; a cyclic amine such as triethylenediamine; an organic sulfonic acid such as p-toluene sulfonic acid, methanesulfonic acid, or fluorosulfuric acid; an inorganic acid such as sulfuric acid, phosphoric acid, or perchloric acid; a base such as sodium alcoholate, lithium hydroxide, aluminum alcoholate, or sodium hydroxide; a titanium compound such as tetrabutyl titanate, tetraethyl titanate, tetraisopropyl titanate; a bismuth compound; or a quaternary ammonium salt. Any one of these examples may be used or any two or more of these examples may be used in combination.

The reaction temperature in the third step can be appropriately selected depending on the objective, without any specific limitations, and is preferably from 40° C. to 90° C.

from a viewpoint of reaction efficiency and prevention of thermopolymerization of acrylic groups.

In a synthetic method of a conventional surface-modifying agent having a perfluoropolyether chain and a (meth) acrylate group, a compound that does not include one out of the perfluoropolyether chain and the (meth)acrylate group is produced as a by-product. In contrast, in the production method of the surface-modifying agent described above, a compound having a perfluoropolyether chain and a compound having a (meth)acrylate group are reacted sequentially, which is advantageous in terms of enabling more accurate synthesis compared to the conventional surface-modifying agent.

<Radiation Curable Resin Composition>

The radiation curable resin composition contains the surface-modifying agent according to the present disclosure. Herein, the term "radiation curable resin composition" refers to a composition that can be cured through irradiation with radiation. The radiation curable resin composition formed through blending with the surface-modifying agent according to the present disclosure can preserve transparency of a substrate while providing the substrate with higher water repellency and higher stain resistance, particularly in terms of wipeability of oil-based ink.

Other components besides the surface-modifying agent according to the present disclosure that are used to prepare the radiation curable resin composition can be appropriately selected depending on the objective, without any specific limitations, and can for example include a polymerizable monomer or a polymerizable resin.

—Polymerizable Monomer—

The polymerizable monomer may be a monofunctional monomer or a polyfunctional monomer.

The monofunctional monomer can be appropriately selected depending on the objective, without any specific limitations, and may for example be N-vinylcaprolactam, N-vinylpyrrolidone, N-vinylcarbazole, vinylpyridine, acrylamide, N,N-dimethyl (meth)acrylamide, isobutoxymethyl (meth)acrylamide, t-octyl (meth)acrylamide, diacetone (meth)acrylamide, dimethylaminoethyl (meth)acrylate, diethylaminoethyl (meth)acrylate, 7-amino-3,7-dimethyloctyl (meth)acrylate, acrylolylmorpholine, lauryl (meth)acrylate, dicyclopentadienyl (meth)acrylate, dicyclopentenyloxyethyl (meth)acrylate, dicyclopentenyl (meth)acrylate, tetrahydrofurfuryl (meth)acrylate, ethylene diethylene glycol (meth)acrylate, butoxyethyl (meth)acrylate, methyl triethylene diglycol (meth)acrylate, and phenoxyethyl (meth) acrylate. Any one of these examples may be used or any two or more of these examples may be used in combination.

The polyfunctional monomer can be appropriately selected depending on the objective, without any specific limitations, and may for example be trimethylolpropane tri(meth)acrylate, triethyleneoxide-modified trimethylolpropane tri(meth)acrylate, tripropyleneoxide-modified glycerin tri(meth)acrylate, triethyleneoxide-modified glycerin tri (meth)acrylate, triepichlorohydrin-modified glycerin tri (meth)acrylate, 1,3,5-triacroylhexahydro-s-triazine, tris (acryloyloxyethyl)isocyanurate, pentaerythritol tri(meth) acrylate, pentaerythritol tetra(meth)acrylate, tetraethyleneoxide-modified pentaerythritol tetra(meth) acrylate, ditrimethylolpropane tetra(meth)acrylate, diethyleneoxide-modified ditrimethylolpropane tetra(meth)acrylate, dipentaerythritol penta(meth)acrylate, alkyl-modified dipentaerythritol pentaacrylate, alkyl-modified dipentaerythritol tetraacrylate, ε-caprolactone-modified dipentaerythritol hexa(meth)acrylate, dipentaerythritol penta(meth)acrylate, dipentaerythritol hexa(meth)acrylate, hexaethyleneoxide-modified sorbitol hexa(meth)acrylate, and hexakis(methacryloyloxyethyl)cyclotriphosphazene. Any one of these examples may be used or any two or more of these examples may be used in combination.

—Polymerizable Resin—

The polymerizable resin can be appropriately selected depending on the objective, without any specific limitations, and is for example an epoxy (meth)acrylate obtained through a reaction between a compound having a plurality of glycidyl groups and (meth)acrylic acid; or an urethane (meth)acrylate obtained through a reaction between an aliphatic or aromatic polyisocyanate and a (meth)acrylate having a hydroxy group. Any one of these examples may be used or any two or more of these examples may be used in combination.

—Other Materials—

Other materials that can be used in the radiation curable resin composition and that can be appropriately selected depending on the objective, without any specific limitations, include various organic solvents, various resins, various organic particles, various inorganic particles, polymerization initiators, polymerization inhibitors, antistatic agents, defoamers, viscosity modifiers, light stabilizers, weathering stabilizers, heat stabilizers, antioxidants, rust inhibitors, slip agents, waxes, gloss modifiers, mold release agents, compatibilizers, conduction modifiers, pigments, dyes, dispersants, dispersion stabilizers, and surfactants. Any one of these examples may be used or any two or more of these examples may be used in combination.

The blended amount of the surface-modifying agent in the radiation curable resin composition can be appropriately selected depending on the objective, without any specific limitations, and is preferably from 0.01 parts by mass to 2 parts by mass, and more preferably from 0.05 parts by mass to 0.5 parts by mass, in 100 parts by mass of a non-volatile component of the radiation curable resin composition.

It is advantageous for the blended amount to be in either the preferable range or the more preferable range described above in terms of effectively improving stain resistance and preserving transparency.

(Article Using Surface-Modifying Agent)

An article according to the present disclosure can be appropriately selected depending on the objective, without any specific limitations other than that the surface-modifying agent according to the present disclosure is used. For example, the article may be a film that is known in the functional coating industry (for example, a film for anti-reflection, anti-glare, stain-proofing, or abrasion protection) that includes a cured coating film formed by a radiation curable resin composition into which the surface-modifying agent according to the present disclosure has been blended.

Furthermore, the article according to the present disclosure may be an article including a normally transparent substrate surface (for example, plastic or glass) and a cured coating film formed by a radiation curable resin composition into which the surface-modifying agent according to the present disclosure has been blended, or may be an article including a substrate surface of fiber, metal, wood, paper, or the like and including a cured coating film formed by a radiation curable resin composition into which the surface-modifying agent according to the present disclosure has been blended.

EXAMPLES

The following provides a more specific explanation of the present disclosure through examples and comparative examples. However, the present disclosure is not limited to the following examples.

Example 1

Preparation of Surface-Modifying Agent (A)

A 500-mL flask was charged with 7.58 g of cyanuric chloride, 4.99 g of collidine, and 110 g of toluene, and was stirred in an ice bath to reach a liquid temperature of 5° C. or lower. The resultant solution was maintained at 5° C. or lower while dripping in a separately prepared mixed solution including 45 g of a perfluoropolyether (Fluorolink D produced by Solvay Specialty Polymers Japan K.K., number-average molecular weight 2,190) and 220 g of a hydrofluoroether (Novec 7200 produced by 3M, $C_4F_9$—O—$C_2H_5$) as a solvent over a period of 4 hours. Thereafter, the flask was removed from the ice bath and was stirred for 3 hours at room temperature. The resultant reaction liquid was concentrated using an evaporator to obtain a residue that was subsequently washed three times with 100 g of toluene. Thereafter, the residue was washed three times with 100 g of methyl ethyl ketone (produced by Wako Pure Chemical Industries, Ltd.) to obtain a transparent yellow viscous liquid. The resultant viscous liquid was dried for 16 hours at 40° C. using a vacuum dryer to yield 40 g (79% yield) of a transparent yellow viscous liquid (intermediate compound 1).

Next, a 100-mL flask equipped with a reflux condenser was charged with 8.51 g of the transparent yellow viscous liquid (intermediate compound 1) and 11.5 g of diethanolamine (produced by Wako Pure Chemical Industries, Ltd.), and was stirred for 1 hour under air cooling while carrying out an exothermic reaction. Once heat generation had subsided, the flask was heated and was stirred for 3 hours at 45° C. Thereafter, stirring was performed for a further 6 hours at 100° C. Next, cooling was performed to room temperature, 45 g of methanol (produced by Wako Pure Chemical Industries, Ltd.) was added to the flask, and a methanol portion was removed by decantation. Decantation was performed twice more in the same manner. The resultant residue was dried for 18 hours at 65° C. using a vacuum dryer to yield 6.7 g (70% yield) of a transparent colorless viscous liquid (intermediate compound 2).

Next, a 100-mL flask equipped with a reflux condenser was charged with 1.5 g of the transparent colorless viscous liquid (intermediate compound 2), 2 g of methyl ethyl ketone (produced by Wako Pure Chemical Industries, Ltd.), 0.0016 g of dibutyltin dilaurate (produced by Wako Pure Chemical Industries, Ltd.), and 0.492 g of 2-acryloyloxyethyl isocyanate (Karenz AOI produced by Showa Denko K.K.), and was stirred for 10 hours at 60° C. Thereafter, cooling was performed to room temperature and concentrating was performed using an evaporator. Next, 10 g of methanol (produced by Wako Pure Chemical Industries, Ltd.) was added to the resultant residue and a methanol portion was removed by decantation after sufficient stirring. Decantation was performed twice more in the same manner. The resultant residue was dried for 8 hours at 40° C. using a vacuum dryer to yield a target compound (surface-modifying agent (A)) in a colorless and waxy state (94% yield).

The following spectra were obtained as a result of performing spectral analysis of the obtained surface-modifying agent (A) by NMR (MERCURY 300 produced by Varian Inc.) and FT-IR (FT/IR460plus produced by JASCO corporation).

[FT-IR Spectrum]
  1200 $cm^{-1}$: C—F
  1530 $cm^{-1}$: Acrylic group

[$^1$H-NMR Spectrum]
  (ppm, 300 MHz, solvent: acetone-$d_6$, standard: tetramethylsilane (TMS))
  3.40 ppm (8H, m)
  3.67 ppm to 3.91 ppm (8H, m)
  4.17 ppm (8H, t, J=5.4 Hz)
  4.20 ppm to 4.34 ppm (8H, m)
  4.88 ppm (2H, m)
  5.85 ppm (4H, dd, J=1.8 Hz, 10.2 Hz)
  6.10 ppm (4H, dd, J=10.2 Hz, 17.4 Hz)
  6.34 ppm (4H, dd, J=1.8 Hz, 17.4 Hz)
  6.56 ppm to 6.66 ppm (4H, m)

FIG. 1 is a chart of the $^1$H-NMR spectrum for the surface-modifying agent (A).

From these analytical results, the surface-modifying agent (A) was identified to have a structure indicated by formula (4) shown below. Herein, m/n was 1.09, and a perfluoropolyether chain part sandwiched between two $CF_2$ groups in formula (4) shown below had a number-average molecular weight of 2,190. The surface-modifying agent (A) had a weight-average molecular weight (measured by GPC using polystyrene as a reference material) of 3,300.

[CHEM 7]

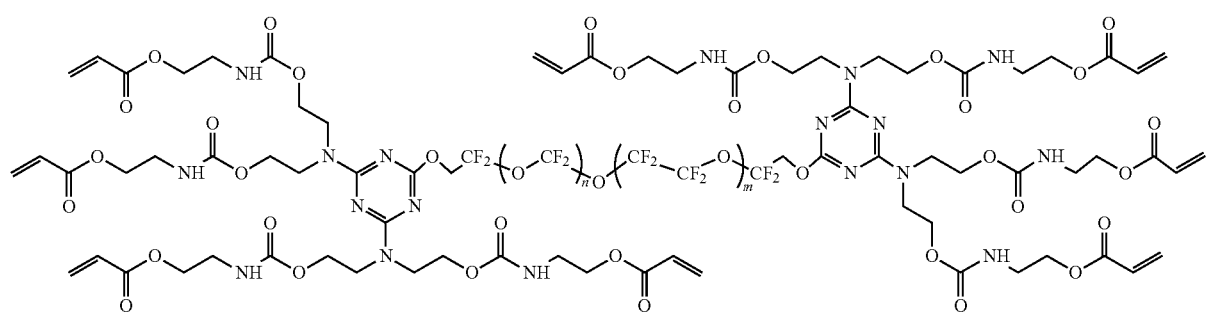

(4)

Example 2

Preparation of Surface-Modifying Agent (B)

A 500-mL flask was charged with 5.81 g of cyanuric chloride, 3.82 g of collidine, and 150 g of toluene and was stirred in an ice bath to reach a liquid temperature of 5° C. or lower. The resultant solution was maintained at 5° C. or lower while dripping in a separately prepared mixed solution including 38.2 g of a perfluoropolyether (Fluorolink D4000 produced by Solvay Specialty Polymers Japan K.K., number-average molecular weight 3,800) and 370 g of a hydrofluoroether (Novec 7200 produced by 3M, $C_4F_9$—O—$C_2H_5$) as a solvent over a period of 4 hours. Thereafter, the flask was removed from the ice bath and was stirred for 3 hours at room temperature. The resultant reaction liquid was concentrated using an evaporator to obtain a residue that was subsequently washed three times with 100 g of toluene. Thereafter, the residue was washed three times with 100 g of methyl ethyl ketone (produced by Wako Pure Chemical Industries, Ltd.) to obtain a yellow viscous liquid. The resultant viscous liquid was dried for 16 hours at 40° C. using a vacuum dryer to yield 24 g (89% yield) of a transparent yellow viscous liquid (intermediate compound 1).

Next, a 300-mL flask equipped with a reflux condenser was charged with 30.1 g of the transparent yellow viscous liquid (intermediate compound 1) and 24.9 g of diethanolamine (produced by Wako Pure Chemical Industries, Ltd.), and was stirred for 1 hour under air cooling while carrying out an exothermic reaction. Once heat generation had subsided, the flask was heated and was stirred for 3 hours at 45° C. Thereafter, stirring was performed for a further 24 hours at 100° C. Next, cooling was performed to room temperature, 95 g of methanol (produced by Wako Pure Chemical Industries, Ltd.) was added to the flask, and a methanol portion was removed by decantation. Decantation was performed twice more in the same manner. The resultant residue was dried for 18 hours at 65° C. using a vacuum dryer to yield 27.7 g (87% yield) of a transparent colorless viscous liquid (intermediate compound 2).

Next, a 100-mL flask equipped with a reflux condenser was charged with 2.09 g of the transparent colorless viscous liquid (intermediate compound 2), 3 g of methyl ethyl ketone (produced by Wako Pure Chemical Industries, Ltd.), 0.0048 g of dibutyltin dilaurate (produced by Wako Pure Chemical Industries, Ltd.), and 0.45 g of 1,1-(bisacryloyloxymethyl)ethyl isocyanate (Karenz BEI produced by Showa Denko K.K.), and was stirred for 10 hours at 60° C. Thereafter, cooling was performed to room temperature and concentrating was performed using an evaporator. Next, 20 g of methanol (produced by Wako Pure Chemical Industries, Ltd.) was added to the resultant residue and a methanol portion was removed by decantation after sufficient stirring. Decantation was performed twice more in the same manner. The resultant residue was dried for 8 hours at 40° C. using a vacuum dryer to yield 1.64 g (55% yield) of a target compound (surface-modifying agent (B)) in a colorless and waxy state.

The following spectra were obtained as a result of performing spectral analysis of the obtained surface-modifying agent (B) in the same way as in Example 1.

[FT-IR Spectrum]
 1200 $cm^{-1}$: C—F
 1530 $cm^{-1}$: Acrylic group

[$^1$H-NMR Spectrum]
 (ppm, 300 MHz, solvent: acetone-$d_6$, standard: tetramethylsilane (TMS))
 1.40 ppm (24H, s)
 3.72 ppm to 3.81 ppm (16H, m)
 4.17 ppm to 4.26 ppm (16H, m)
 4.36 ppm (32H, s)
 4.86 ppm to 4.98 ppm (4H, m)
 5.89 ppm (16H, dd, J=1.8 Hz, 10.2 Hz)
 6.22 ppm (H, dd, J=10.2 Hz, 17.1 Hz)
 6.37 ppm (H, dd, J=1.8 Hz, 17.1 Hz)
 6.40 ppm to 6.48 ppm (8H, m)

Figure 2:
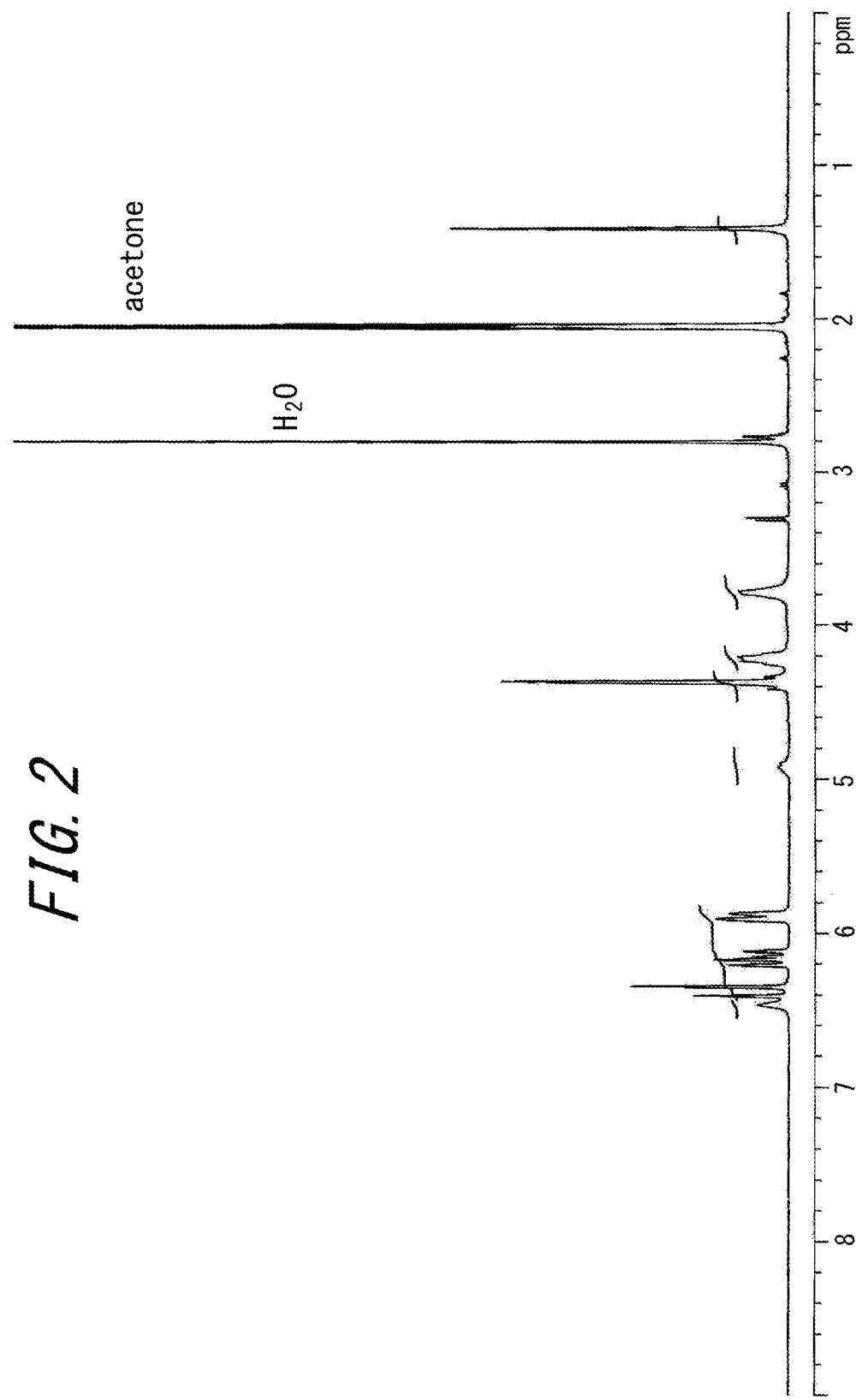
FIG. 2 is a chart of a $^1$H-NMR spectrum for a surface-modifying agent (B) in Example 2.

FIG. 2 is a chart of the $^1$H-NMR spectrum for the surface-modifying agent (B).

From these analytical results, the surface-modifying agent (B) was identified to have a structure indicated by formula (5) shown below. Herein, m/n was 0.94, and a perfluoropolyether chain part sandwiched between two $CF_2$ groups in formula (5) shown below had a number-average molecular weight of 3,800. The surface-modifying agent (B) had a weight-average molecular weight (measured by GPC using polystyrene as a reference material) of 5,900.

[CHEM 8]

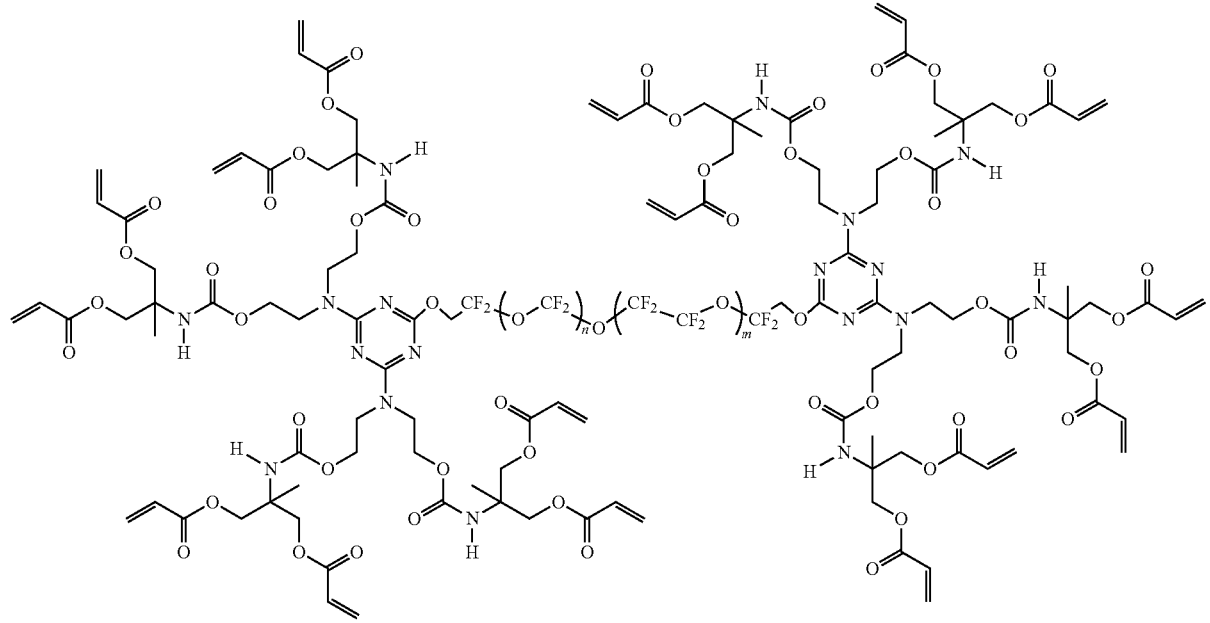

(5)

Comparative Example 1

Preparation of Surface-Modifying Agent (C)

A 100-mL flask was charged with 5.84 g of HDI isocyanurate (Sumidur N3300 produced by Sumika Bayer Urethane Co., Ltd., NCO % 22.6%), 0.013 g of dibutyltin dilaurate, and 28.7 g of methyl ethyl ketone, and stirring was initiated. Thereafter, 10.95 g of a perfluoropolyether (Fluorolink D produced by Solvay Specialty Polymers Japan K.K., number-average molecular weight 2,190) was dripped into the resultant solution at room temperature. After this dripping, stirring was performed for 3 hours at 60° C. Next, 2.32 g of 2-hydroxyethyl acrylate (produced by Tokyo Chemical Industry Co., Ltd.) was dripped into the resultant solution and stirring was performed for 18 hours at 60° C. (the end point of the reaction was determined to be a time at which absorption due to an isocyanate group could no longer be confirmed in FT-IR analysis). Thereafter, cooling was performed to room temperature to yield a surface-modifying agent (C) as a transparent, pale yellow viscous liquid (fluorine-containing compound solution, non-volatile content 40%).

The following spectrum was obtained as a result of performing FT-IR analysis of the obtained surface-modifying agent (C) in the same way as in Example 1.

[FT-IR Spectrum]
- 3385 $cm^{-1}$: N—H
- 2944 $cm^{-1}$: C—H
- 2913 $cm^{-1}$: C—H
- 1724 $cm^{-1}$: Ester carbonyl group
- 1690 $cm^{-1}$: Isocyanurate ring
- 1639 $cm^{-1}$: Acrylic group
- 1632 $cm^{-1}$: Acrylic group
- 1540 $cm^{-1}$: Carbamoyl group
- 1470 $cm^{-1}$: Carbamoyl group
- 1207 $cm^{-1}$: C—F From these analytical results, the surface-modifying agent (C) was identified to have a structure indicated by formula (6) shown below. Herein, m/n was 1.09, and a perfluoropolyether chain part sandwiched between two $CF_2$ groups in formula (6) shown below had a number-average molecular weight of 2,190.

Comparative Example 2

Preparation of Surface-Modifying Agent (D)

A 100-mL flask was charged with 4.67 g of HDI isocyanurate (Sumidur N3300 produced by Sumika Bayer Urethane Co., Ltd., NCO % 22.6%), 0.024 g of dibutyltin dilaurate, and 18.2 g of methyl ethyl ketone, and stirring was initiated. Next, 5.60 g of a perfluoropolyether (Fluorolink D10H produced by Solvay Specialty Polymers Japan K.K., number-average molecular weight 1,400) was dripped into the resultant solution at room temperature. After this dripping, stirring was performed for 3 hours at 60° C. Next, 1.86 g of 2-hydroxyethyl acrylate (produced by Tokyo Chemical Industry Co., Ltd.) was dripped into the resultant solution and stirring was performed for 18 hours at 60° C. (the end point of the reaction was determined to be a time at which absorption due to an isocyanate group could no longer be confirmed in FT-IR analysis). Thereafter, cooling was performed to room temperature to yield a surface-modifying agent (D) as a transparent, pale yellow viscous liquid (fluorine-containing compound solution, non-volatile content 40%).

The following spectrum was obtained as a result of performing FT-IR analysis of the obtained surface-modifying agent (D) in the same way as in Example 1.

[FT-IR Spectrum]
- 3385 $cm^{-1}$: N—H
- 2944 $cm^{-1}$: C—H
- 2913 $cm^{-1}$: C—H
- 1724 $cm^{-1}$: Ester carbonyl group
- 1690 $cm^{-1}$: Isocyanurate ring
- 1639 $cm^{-1}$: Acrylic group
- 1632 $cm^{-1}$: Acrylic group
- 1540 $cm^{-1}$: Carbamoyl group
- 1470 $cm^{-1}$: Carbamoyl group
- 1207 $cm^{-1}$: C—F From these analytical results, the surface-modifying agent (D) was identified to have a structure indicated by formula (6) shown above. Herein, m/n was 1.80, and the perfluoropolyether chain part sandwiched between two $CF_2$ groups in formula (6) shown above had a number-average molecular weight of 1,400.

<Preparation of Radiation Curable Resin Composition>

A radiation curable resin composition was prepared for each of the surface-modifying agents (A) to (D) by adding the surface-modifying agent to a mixture including 79 mass % (85 parts by mass) of PETIA (mixture composed mainly of pentaerythritol triacrylate and pentaerythritol tetraacrylate) produced by Daicel Allnex, Ltd., 14 mass % (15 parts by mass) of OTA-480 (mixture composed mainly of propylene glycol-modified glycerin triacrylate) produced by Daicel Allnex, Ltd., 5 mass % (5 parts by mass) of AE-400 (polyethylene glycol monoacrylate) produced by NOF Corporation, and 2 mass % (3 parts by mass) of IRGACURE 184 (1-hydroxycyclohexyl phenyl ketone) produced by BASF. The surface-modifying agent was added as non-volatile content of 0.2 parts by mass relative to 100 parts by mass of the aforementioned mixture.

<Preparation of Cured Coating Film>

A cured coating film was obtained by applying the radiation curable resin composition onto a PET film (product name: Lumirror U48, produced by Toray Industries, Inc., thickness 100 m) with a film thickness of 8 m (wet thickness) and irradiating the radiation curable resin composition

[CHEM 9]

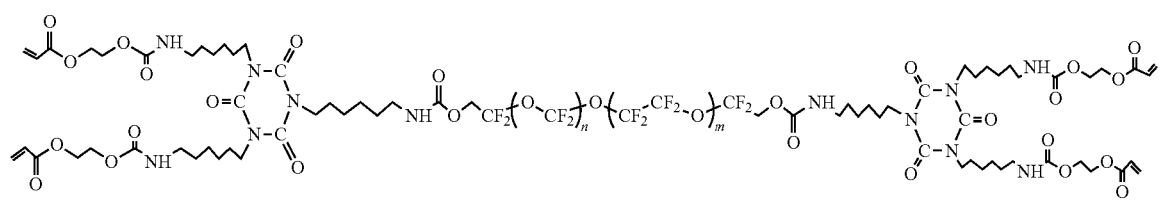

(6)

with radiation of 1500 mJ/cm² in a nitrogen atmosphere using an alignment light exposure device produced by Toshiba Lighting & Technology Corporation. The cured coating film was evaluated as described below. The following evaluations were also carried out on a PET film (product name: Lumirror U48, produced by Toray Industries, Inc., thickness 100 m) on which a cured coating film had not been formed, which was used as a reference example.

<Evaluation>
(Evaluation of External Appearance)

The color and transparency of the surface of the cured coating film on the PET film were visually evaluated.

(Contact Angle)

A contact angle meter DM-701 produced by Kyowa Interface Science Co., Ltd. was used to measure the contact angle of water and the contact angle of hexadecane on the surface of the cured coating film. Note that for the purpose of reference, the contact angle of water and the contact angle of hexadecane were also measured for the PET film on which a cured coating film had not been formed. A high contact angle for water indicates excellent water repellency and a high contact angle for hexadecane indicates excellent oil repellency.

(Surface Free Energy)

The contact angle measurement results described above were used to measure the surface free energy at the surface of the cured coating film by the Kaelble-Wu method. A low value for the surface free energy indicates excellent water repellency/oil repellency.

(Evaluation of Oil-Based Ink Adhesion)

An oil-based pen (Mckee produced by Zebra Co., Ltd.) was used to perform test-writing on the surface of the cured coating film and ink adhesion was subsequently visually inspected. An evaluation of good was given when the ink was repelled and aggregated in a particle shape and an evaluation of poor was given when the ink adhered to the surface without aggregating.

(Evaluation of Oil-Based Ink Wipeability and Dynamic Coefficient of Friction During Wiping)

Non-woven fabric (BEMCOT produced by Asahi Kasei Corporation) was used to perform wiping once, in a single direction, with respect to the oil-based ink on the surface of the cured coating film after evaluation of oil-based ink adhesion, and ink adhesion was visually inspected after the wiping. An evaluation of good was given when the ink was cleanly wiped off, an evaluation of mediocre was given when some of the ink was wiped off and some of the ink was smeared without being wiped off, and an evaluation of poor was given when almost none of the ink was wiped off.

A tribometer TS-501 produced by Kyowa Interface Science Co., Ltd. was used to measure the dynamic coefficient of friction between the surface of the cured coating film and the non-woven fabric during the wiping. A small dynamic coefficient of friction indicates that ink is smoothly wiped off.

Ink adhesion before and after wiping is illustrated in FIGS. 3-7 for the reference example, Example 1, Example 2, Comparative Example 1, and Comparative Example 2, respectively. In each of FIGS. 3-7, ink adhesion before wiping is shown on the left and ink adhesion after wiping is shown on the right.

The results of the various evaluations described above are shown in Table 1.

TABLE 1

|  | Reference example | Example 1 | Example 2 | Comparative Example 1 | Comparative Example 2 |
| --- | --- | --- | --- | --- | --- |
| Coating with composition | No | Yes | Yes | Yes | Yes |
| Surface-modifying agent | — | (A) | (B) | (C) | (D) |
| Surface appearance | Transparent colorless | Transparent colorless | Transparent colorless | Transparent colorless | Transparent colorless |
| Water contact angle (°) | 71 | 112 | 111 | 111 | 110 |
| Hexadecane contact angle (°) | 6.4 | 62 | 62 | 63 | 64 |
| Surface free energy (mJ/m²) | 38.8 | 15.4 | 15.6 | 15.2 | 15.2 |
| Evaluation of oil-based ink adhesion | Poor | Good | Good | Good | Good |
| Evaluation of oil-based ink wiping | Poor | Good | Good | Mediocre | Poor |
| Dynamic coefficient of friction | 0.682 | 0.214 | 0.220 | 0.303 | 0.384 |

Through comparison of the evaluation results for the reference example, Examples 1 and 2, and Comparative Examples 1 and 2 shown in Table 1, it can be determined that when a composition containing the surface-modifying agent according to the present disclosure is applied onto the surface of a PET film and is cured thereon, transparency can be preserved to the same level as when a conventional surface-modifying agent is used while also increasing the contact angles for water and hexadecane, and lowering the surface free energy. Also, with regard to adhesion of oil-based ink to the surface of a cured coating film, the results demonstrate that when the surface-modifying agent according to the present disclosure is used, the ink is repelled and aggregates in a particle shape to the same level as when a conventional surface-modifying agent is used.

Furthermore, through comparison of the evaluation results for the reference example in Table 1 with the evaluation results for Examples 1 and 2 and Comparative Examples 1 and 2, and through comparison of ink adhesion illustrated in FIGS. 3-7, it can be determined that when the surface-modifying agent according to the present disclosure is used, not only can ink be wiped off more smoothly than when a conventional surface-modifying agent is used because the dynamic coefficient of friction between the cured coating film surface and non-woven fabric during wiping is lower, but also ink can be wiped off cleanly through a single wipe.

INDUSTRIAL APPLICABILITY

The surface-modifying agent according to the present disclosure can be suitably used for films that are known in the functional coating industry (for example, films for anti-reflection, anti-glare, stain-proofing, or abrasion protection), can be used for articles having a normally transparent substrate surface (for example, plastic or glass), and can also be used for articles having a substrate surface such as fiber, metal, wood, or paper.

The invention claimed is:

1. A surface-modifying agent comprising:
   a triazine skeleton;
   a (meth)acrylate group bonded to the triazine skeleton via an urethane bond; and
   a perfluoropolyether chain bonded to the triazine skeleton, wherein
   the surface-modifying agent is represented by formula (1) or (2) shown below,

[CHEM 1]

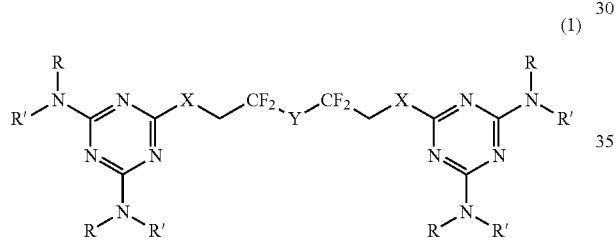
(1)

[CHEM 2]

(2)

Z—Y—CF$_2$—X—[triazine with R, R' groups]

where, in the formulae (1) and (2):
—X— represents —O—, —N(R$^1$)—, or —O—CH$_2$CH$_2$—O—, wherein R$^1$ represents hydrogen or an alkyl group;
—Y— represents a perfluoropolyether chain selected from the group consisting of —(OCF$_2$)$_n$—O—(CF$_2$CF$_2$O)$_m$—, —O—(CF$_2$CF$_2$O)$_p$—, —O—(CF$_2$CF$_2$CF$_2$O)$_q$—, and —O—(CF(CF$_3$)CF$_2$C)$_r$—, wherein m, n, p, q, and r each represent a positive integer, 0.8<m/n<3 is satisfied, and units composing —Y— may be bonded to one another in any order;
R and R' may represent the same or different structures each indicated by hydrogen, an alkyl group having a carbon number of 1-8, or —R$^2$—O—CO—NH—R$^3$, with at least one of R and R' being a structure indicated by —R$^2$—O—CO—NH—R$^3$, wherein R$^2$ represents an alkylene group having a carbon number of 2-8 and having a chain, branched, or ring shape, and R$^3$ represents —CH$_2$CH$_2$—OCO—CH=CH$_2$, —CH$_2$CH$_2$—OCO—C(CH$_3$)=CH$_2$, or —C(CH$_3$)—(CH$_2$—OCO—CH=CH$_2$)$_2$; and
Z— represents CF$_3$—, CF$_3$—CF$_2$—O—, CF$_3$—CF$_2$—CF$_2$—, or CF$_3$—CF(CF$_3$)—O—.

2. The surface-modifying agent of claim 1, wherein separate triazine skeletons are bonded to opposite ends of the perfluoropolyether chain.

3. The surface-modifying agent of claim 1, wherein the perfluoropolyether chain represented by Y has a number-average molecular weight of 1,000 to 5,000.

4. The surface modifying agent of claim 1 represented by formula (3) shown below,

[CHEM 3]

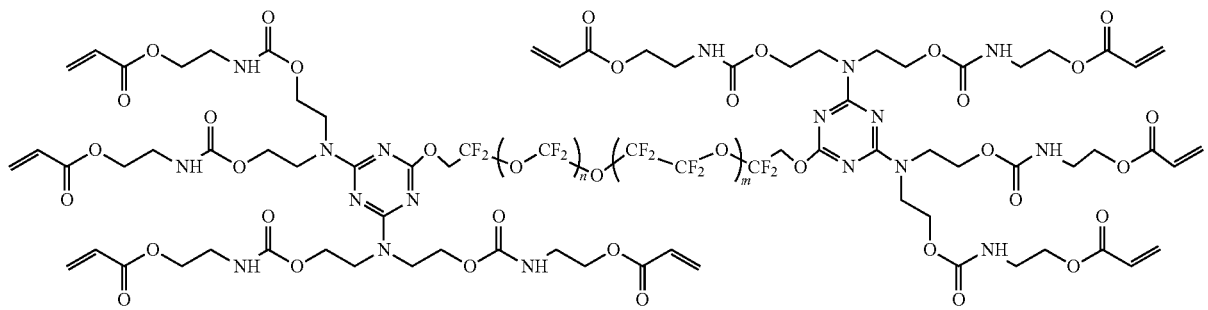
(3)

where, in the formula (3), m and n each represent a positive integer, 0.8<m/n<3 is satisfied, and —(OCF$_2$)—, —O—, and —(CF$_2$CF$_2$O)— composing —(OCF$_2$)$_n$—O—(CF$_2$CF$_2$O)$_m$— in the formula (3) may be bonded to one another in any order.

5. An article comprising the surface-modifying agent of claim 1.

* * * * *